(12) United States Patent
Dolan et al.

(10) Patent No.: US 10,639,583 B2
(45) Date of Patent: May 5, 2020

(54) ADSORBENT FOR HYDROCARBON RECOVERY

(71) Applicant: BASF Corporation, Florham Park, NJ (US)

(72) Inventors: William B. Dolan, Yardley, PA (US); Roger Wyatt, West Midlands (GB); Angela Siegel, Hannover (DE); Klaus Neumann, Sehnde (DE); Tobias Eckardt, Hildesheim (DE)

(73) Assignee: BASF Corporation, Florham Park, NJ (US)

( * ) Notice: Subject to any disclaimer, the term of this patent is extended or adjusted under 35 U.S.C. 154(b) by 100 days.

(21) Appl. No.: 15/737,192

(22) PCT Filed: Jun. 17, 2016

(86) PCT No.: PCT/US2016/038038
§ 371 (c)(1),
(2) Date: Dec. 15, 2017

(87) PCT Pub. No.: WO2016/205616
PCT Pub. Date: Dec. 22, 2016

(65) Prior Publication Data
US 2018/0221809 A1  Aug. 9, 2018

Related U.S. Application Data

(60) Provisional application No. 62/180,805, filed on Jun. 17, 2015.

(51) Int. Cl.
*B01D 53/047* (2006.01)
*C10L 3/10* (2006.01)
(Continued)

(52) U.S. Cl.
CPC ......... *B01D 53/0462* (2013.01); *B01D 53/02* (2013.01); *B01D 53/72* (2013.01);
(Continued)

(58) Field of Classification Search
CPC .... B01D 53/02; B01D 53/04; B01D 53/0462; B01D 53/72; B01D 2253/106; B01D 2253/306; B01D 2253/308; B01D 2256/245; B01D 2257/702; B01J 20/103; B01J 20/28004; B01J 20/28011; B01J 20/28014; B01J 20/28019; B01J 20/28054; B01J 20/28064; B01J 20/28069; B01J 20/28071; B01J 20/28085; B01J 20/3433;
(Continued)

(56) References Cited

U.S. PATENT DOCUMENTS 5,338,450 A * 8/1994 Maurer ............... B01D 53/0446
210/286
6,171,370 B1 1/2001 Hirano et al.
(Continued)

OTHER PUBLICATIONS

International Search Report and Written Opinion of the International Search Authority dated Sep. 13, 2016 for International Application No. PCT/US2016/38038, 12 pages.

*Primary Examiner* — Frank M Lawrence, Jr.
(74) *Attorney, Agent, or Firm* — Lowenstein Sandler LLP

(57) ABSTRACT

Disclosed in certain embodiments are sorbents for capturing heavy hydrocarbons via thermal swing adsorption processes.

17 Claims, 1 Drawing Sheet

(51) Int. Cl.

| | |
|---|---|
| *B01D 53/04* | (2006.01) |
| *B01J 20/28* | (2006.01) |
| *B01J 20/10* | (2006.01) |
| *B01J 20/34* | (2006.01) |
| *B01D 53/02* | (2006.01) |
| *C07C 7/12* | (2006.01) |
| *B01D 53/72* | (2006.01) |

(52) U.S. Cl.
CPC ....... *B01J 20/103* (2013.01); *B01J 20/28004* (2013.01); *B01J 20/28011* (2013.01); *B01J 20/28014* (2013.01); *B01J 20/28019* (2013.01); *B01J 20/28054* (2013.01); *B01J 20/28064* (2013.01); *B01J 20/28069* (2013.01); *B01J 20/28071* (2013.01); *B01J 20/28085* (2013.01); *B01J 20/3433* (2013.01); *B01J 20/3458* (2013.01); *C07C 7/12* (2013.01); *C10L 3/10* (2013.01); *C10L 3/101* (2013.01); *B01D 2253/106* (2013.01); *B01D 2253/306* (2013.01); *B01D 2253/308* (2013.01); *B01D 2256/245* (2013.01); *B01D 2257/702* (2013.01); *B01J 2220/56* (2013.01)

(58) Field of Classification Search
CPC ..... B01J 20/3458; B01J 2220/56; C07C 7/12; C10L 3/10; C10L 3/101
USPC ................ 95/90, 143, 147; 96/108; 585/820
See application file for complete search history.

(56) References Cited

U.S. PATENT DOCUMENTS

| 6,514,317 | B2 | 2/2003 | Hirano et al. | |
|---|---|---|---|---|
| 2003/0047071 | A1* | 3/2003 | Dolan | B01D 53/047 95/96 |
| 2003/0172808 | A1* | 9/2003 | Le Bec | C01B 3/56 95/96 |
| 2004/0220046 | A1 | 11/2004 | Stockwell et al. | |
| 2007/0006729 | A1* | 1/2007 | Mitariten | B01D 53/0462 95/92 |
| 2007/0123595 | A1 | 5/2007 | Lowe et al. | |
| 2008/0216391 | A1 | 9/2008 | Cortright et al. | |
| 2009/0151562 | A1* | 6/2009 | Russell | B01D 53/02 95/143 |
| 2013/0291723 | A1* | 11/2013 | Zhou | B01D 53/02 95/144 |

\* cited by examiner

ADSORBENT FOR HYDROCARBON RECOVERY

CROSS-REFERENCE TO RELATED APPLICATION

This application is a national stage entry under 35 U.S.C. § 371 of International Application Serial No. PCT/US2016/038038, filed on Jun. 17, 2016, which claims the benefit of priority of U.S. Provisional Patent Application Ser. No. 62/180,805, filed on Jun. 17, 2015, the disclosures of which are hereby incorporated by reference herein in their entireties.

BACKGROUND

Hydrocarbons are commonly removed from natural gas to prevent the condensation of liquids in pipeline transmission systems. Pipelines commonly impose a dew point specification to prevent the condensation of the liquids, with hydrocarbon recovery units (HRUs) being utilized to remove heavy hydrocarbons in particular.

Silica gel sorbents have an affinity for heavy hydrocarbons, such as C6+ components, and may be used in HRUs. In such systems, a fluid volume (e.g., natural gas) containing heavy hydrocarbons is passed through a bed of silica gel to trap heavy hydrocarbons. Regeneration may be performed by passing a pressurized and/or heated stream of natural gas feed or product gas through the sorbent bed. After cooling, the heavy hydrocarbons contained in the effluent from the regeneration process can be condensed as a liquid product and removed. In order to improve the adsorptive efficiency of such systems, there is a need to explore the use of other sorbent materials that exhibit higher affinities for heavy hydrocarbons.

BRIEF DESCRIPTION OF THE DRAWINGS

The present disclosure is illustrated by way of example, and not by way of limitation, in the figures of the accompanying drawings, in which.

DETAILED DESCRIPTION

Figure 1:
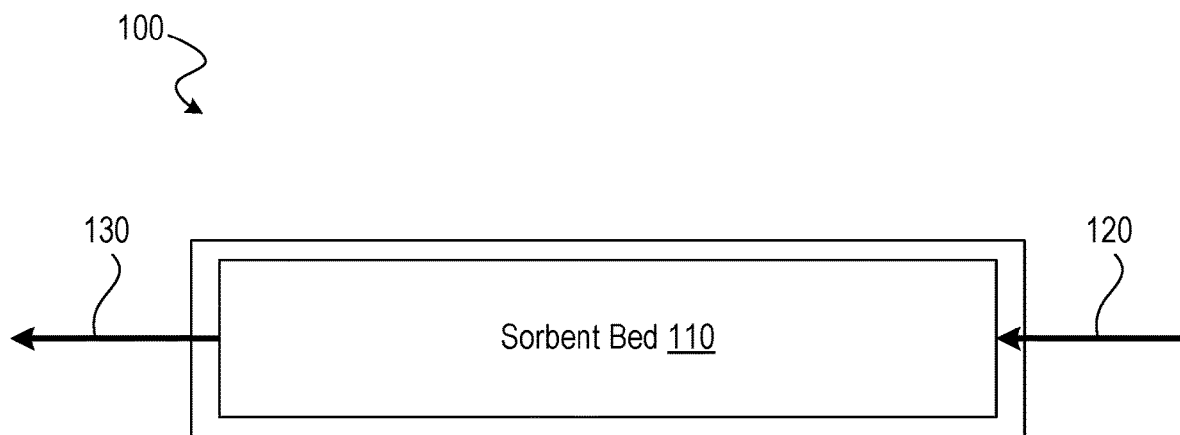
FIG. 1 depicts an illustrative sorbent bed in accordance with an embodiment of the disclosure.

The present disclosure relates generally to a sorbent for improved purification of gas streams, and a system incorporating the sorbent and method of use thereof. More specifically, the present disclosure relates to a sorbent used for the removal of heavy hydrocarbons (e.g., C5+ or C6+ components), water, acid gases, or other chemical species and the recovery of heavy hydrocarbons by use of an integrated process.

The adsorption process of the present disclosure, used to remove heavy hydrocarbons (e.g., C5+ or C6+ components) from fluid volumes (e.g., gas flows), may be accomplished by thermal swing adsorption. Thermal swing adsorption processes are generally known in the art for various types of adsorptive separations. Generally, thermal swing adsorption processes utilize the process steps of adsorption at a low temperature, regeneration at an elevated temperature with a hot purge gas, and a subsequent cooling down to the adsorption temperature. Thermal swing adsorption processes are often used for drying gases and liquids and for purification where trace impurities are to be removed. Thermal swing adsorption processes are often employed when the components to be adsorbed are strongly adsorbed on the adsorbent, and thus heat is required for regeneration.

In a thermal swing adsorption process, the regeneration temperature is typically higher than the adsorption temperature in order to effect desorption of water and higher hydrocarbons. To illustrate, during the first adsorption step, which employs an adsorbent for the adsorption of C5+ or C6+ components from a fluid volume (e.g., a raw natural gas feed stream), the temperature is maintained at less than 150° F. (66° C.) in some embodiments, and from about 60° F. (16° C.) to about 120° F. (49° C.) in other embodiments. In the desorption step of the present disclosure, the C6+ components adsorbed by the sorbent initially are released from the sorbent, thus regenerating the sorbent at temperatures from about 300° F. (149° C.) to about 550° F. (288° C.) in some embodiments.

In this regeneration step, part of one of the fluid volumes (e.g., a stream of natural gas), the product effluent from the adsorption unit, or a waste stream from a downstream process can be heated, and the heated stream is circulated through the adsorbent to desorb the adsorbed components. In some embodiments, it advantageous to employ a hot purge stream comprising a heated raw natural gas stream for regeneration of the adsorbent.

In some embodiments, the pressures used during the adsorption and regeneration steps are generally elevated at typically 800 to 1200 psig. Typically, heavy hydrocarbon adsorption is carried out at pressures close to that of the feed stream and the regeneration steps may be conducted at about the adsorption pressure or at a reduced pressure. When a portion of an adsorption effluent stream is used as a purge gas, the regeneration may be advantageously conducted at about the adsorption pressure, especially when the waste or purge stream is re-introduced into the raw natural gas stream, for example.

FIG. 1 depicts an illustrate system 100 for removing heavy hydrocarbons from a fluid volume. The system 100 includes a sorbent bed 110 that is adapted to receive a fluid volume in a thermal swing adsorption configuration. The fluid volume flows into the sorbent bed 110 via inlet 120, and passes out of the sorbent bed 110 via outlet 130.

In one aspect of the present disclosure, the system 100 includes a sorbent bed comprising a sorbent adapted for adsorption of C5+ or C6+ components from a fluid volume, wherein the sorbent has a composition comprising $SiO_2$ at a first weight percent greater than 99% and $Al_2O_3$ at a second weight percent less than 1%. In some embodiments, other sorbent compositions may be used.

In some embodiments, the sorbent comprises a fluid-accessible surface having a Brunauer-Emmett-Teller (BET) surface area greater than 600 $m^2/g$, greater than 700 $m^2/g$, greater than 600 $m^2/g$ and less than 900 $m^2/g$, or greater than 700 $m^2/g$ and less than 800 $m^2/g$. In such embodiments, the sorbent is adapted to contact the fluid volume such that when the fluid volume has an initial concentration of C6+ components that is greater than 150 ppm, the fluid volume has a final concentration of C6+ components that is less than 10 ppm after the sorbent contacts the fluid volume. In some embodiments, the sorbent comprises a fluid-accessible surface having a BET surface area greater than 725 $m^2/g$ and less than 775 $m^2/g$.

In some embodiments, the sorbent is adapted to contact the fluid volume such that when the fluid volume has an initial concentration of C6+ components that is greater than 150 ppm, the fluid volume has a final concentration of C6+ components that is less than 50 ppm after the sorbent contacts the fluid volume.

In some embodiments, the sorbent is adapted to contact the fluid volume such that when the fluid volume has an initial concentration of C6+ components that is greater than 150 ppm, the fluid volume has a final concentration of C6+ components that is less than 30 ppm after the sorbent contacts the fluid volume.

In some embodiments, the sorbent is adapted to contact the fluid volume such that when the fluid volume has an initial concentration of C6+ components that is greater than 150 ppm, the fluid volume has a final concentration of C6+ components that is less than 20 ppm after the sorbent contacts the fluid volume.

In some embodiments, the sorbent is adapted to contact the fluid volume such that when the fluid volume has an initial concentration of C6+ components that is greater than 150 ppm, the fluid volume has a final concentration of C6+ components that is less than 10 ppm after the sorbent contacts the fluid volume.

In some embodiments, the sorbent is adapted to contact the fluid volume such that when the fluid volume has an initial concentration of C6+ components that is greater than 150 ppm, the fluid volume has a final concentration of C6+ components that is less than 5 ppm after the sorbent contacts the fluid volume.

In some embodiments, the sorbent is adapted to contact the fluid volume such that when the fluid volume has an initial concentration of C6+ components that is greater than 150 ppm, the fluid volume has a final concentration of C6+ components that is less than 2 ppm after the sorbent contacts the fluid volume.

In some embodiments, the sorbent is adapted to contact the fluid volume such that when the fluid volume has an initial concentration of C6+ components that is greater than 150 ppm, the fluid volume has a final concentration of C6+ components that is less than 1 ppm after the sorbent contacts the fluid volume.

In some embodiments, the C6+ components comprise one or more of benzene, heptane, octane, nonane, toluene, or ethylbenzene. In some embodiments, the C6+ components consist essentially of benzene.

In some embodiments, a pore volume (e.g., Barrett-Joyner-Halenda (BJH) pore volume) of the sorbent is greater than 0.40 cm$^3$/g, is greater than 0.40 cm$^3$/g and less than 0.50 cm$^3$/g, or is greater than 0.425 cm$^3$/g and less than 0.475 cm$^3$/g. In some embodiments, a bulk density of the sorbent is less than 600 kg/m$^3$. In some embodiments, the sorbent is in a form of sorbent pellets that form the sorbent bed (e.g., the sorbent bed 110).

In some embodiments, the sorbent is amorphous. In some embodiments, a relative micropore surface area (RMA), which is the ratio of micropore surface area to BET surface area, of the sorbent is greater than 5%, greater than 10%, greater than 15%, greater than 20%, greater than 25%, or greater than 30%. As used herein, "micropore surface area" refers to total surface area associated with pores below 200 Angstroms in diameter.

In some embodiments, a total pore volume for pores between 500 nm and 20000 nm in diameter of the sorbent, as measured via mercury porosimetry, is greater than 5 mm$^3$/g, greater than 10 mm$^3$/g, greater than 20 mm$^3$/g, greater than 30 mm$^3$/g, greater than 40 mm$^3$/g, greater than 45 mm$^3$/g, or greater than 50 mm$^3$/g.

In some embodiments, a mass of the sorbent bed is greater than 22,500 kg and less than 27,500 kg. In such embodiments, a volume of the sorbent bed is greater than 40 m$^3$ and less than 50 m$^3$. In such embodiments, the sorbent is adapted to contact the fluid volume such that when the fluid volume has an initial concentration of C6+ components that is greater than 150 ppm and less than 250 ppm, the fluid volume has a final concentration of C6+ components that is less than 5 ppm after the sorbent contacts the fluid volume.

In some embodiments, a mass of the sorbent bed is greater than 19,000 kg and less than 23,000 kg. In such embodiments, a volume of the sorbent bed is greater than 30 m$^3$ and less than 40 m$^3$. In such embodiments, the sorbent is adapted to contact the fluid volume such that when the fluid volume has an initial concentration of C6+ components that is greater than 150 ppm and less than 250 ppm, the fluid volume has a final concentration of C6+ components that is less than 5 ppm after the sorbent contacts the fluid volume.

In some embodiments, the mass of the sorbent bed is greater than 10,000 kg and less than 15,000 kg. In such embodiments, the volume of the sorbent bed is greater than 6 m$^3$ and less than 10 m$^3$. In such embodiments, the sorbent is adapted to contact the fluid volume such that when the fluid volume has an initial concentration of C6+ components that is greater than 150 ppm and less than 250 ppm, the fluid volume has a final concentration of C6+ components that is less than 35 ppm after the sorbent contacts the fluid volume.

In some embodiments, the system is configured for thermal swing-adsorption.

In another aspect of the present disclosure, a sorbent bed (e.g., sorbent bed 110) is adapted for removal of C6+ components from a fluid volume such that the sorbent bed is capable of reducing a concentration of the C6+ components in the fluid volume from greater than 150 ppm to less than 35 ppm, wherein a bulk density of the sorbent bed is less than 600 kg/m$^3$.

In another aspect of the present disclosure, a sorbent pellet has a composition including SiO$_2$ at a first weight percent greater than 99% and Al$_2$O$_3$ at a second weight percent less than 1%. The sorbent pellet includes a fluid-accessible surface having a BET surface area greater than 700 m$^2$/g, wherein C6+ components are adsorbed to the fluid-accessible surface (e.g., after contacting the sorbent pellet with a fluid volume containing the C6+ components).

In another aspect of the present disclosure, a sorbent is adapted for adsorption of C6+ components, the sorbent having a characteristic selected from a group consisting of: a composition comprising SiO$_2$ at a first weight percent greater than 99% and Al$_2$O$_3$ at a second weight percent less than 1%; a fluid-accessible surface having a BET surface area greater than 700 m$^2$/g; a bulk density of the sorbent that is less than 600 kg/m$^3$; being adapted to adsorb C6+ components from a fluid volume such that a C6+ component concentration of the fluid volume is reduced from greater than 150 ppm to less than 5 ppm; and combinations thereof.

In another aspect of the present disclosure, a method of treating a fluid volume comprises contacting the fluid volume with a sorbent, wherein: the fluid volume has an initial concentration of C6+ components prior to the contacting; and the fluid volume has a final concentration of C6+ components after the contacting that is less than the initial concentration of C6+ components. In some embodiments, the sorbent comprises amorphous SiO$_2$ at a weight percent greater than 80%. In some embodiments, an RMA of the sorbent is greater than 10%. In some embodiments, a total pore volume for pores between 500 nm and 20000 nm in diameter is greater than 10 mm$^3$/g.

In some embodiments, the sorbent comprises amorphous SiO$_2$ at a weight percent greater than 85%, greater than 90%, greater than 95%, greater than 96%, greater than 97%, greater than 98%, or greater than 99%. In some embodiments, the sorbent further comprises $Al_2O_3$ at a weight percent of up to 20% (i.e., from greater than 0% to 20%), up to 15%, up to 10%, up to 9%, up to 8%, up to 7%, up to 6%, up to 5%, up to 4%, up to 3%, up to 2%, or up to 1%.

In some embodiments, the RMA of the sorbent is greater than 15%, greater than 20%, greater than 25%, or greater than 30%. In some embodiments, a micropore surface area of the sorbent is greater than 40 $m^2/g$, greater than 50 $m^2/g$, greater than 100 $m^2/g$, greater than 150 $m^2/g$, greater than 200 $m^2/g$, or greater than 230 $m^2/g$. In some embodiments, the micropore surface area of the sorbent is from 40 $m^2/g$ to 300 $m^2/g$, from 50 $m^2/g$ to 300 $m^2/g$, from 100 $m^2/g$ to 300 $m^2/g$, from 150 $m^2/g$ to 300 $m^2/g$, from 200 $m^2/g$ to 300 $m^2/g$, or from 230 $m^2/g$ to 300 $m^2/g$.

In some embodiments, the total pore volume for pores between 500 nm and 20000 nm in diameter is greater than 20 $mm^3/g$, greater than 40 $mm^3/g$, greater than 70 $mm^3/g$, greater than 100 $mm^3/g$, greater than 120 $mm^3/g$, greater than 140 $mm^3/g$, greater than 150 $mm^3/g$, greater than 160 $mm^3/g$, or greater than 170 $mm^3/g$. In some embodiments, the total pore volume for pores between 500 nm and 20000 nm in diameter is from 20 $mm^3/g$ to 200 $mm^3/g$, from 40 $mm^3/g$ to 200 $mm^3/g$, from 70 $mm^3/g$ to 200 $mm^3/g$, from 100 $mm^3/g$ to 200 $mm^3/g$, from 120 $mm^3/g$ to 200 $mm^3/g$, from 140 $mm^3/g$ to 200 $mm^3/g$, from 150 $mm^3/g$ to 200 $mm^3/g$, from 160 $mm^3/g$ to 200 $mm^3/g$, or from 170 $mm^3/g$ to 200 $mm^3/g$.

In some embodiments, the sorbent comprises a fluid-accessible surface having a BET surface area greater than 400 $m^2/g$, greater than 500 $m^2/g$, greater than 600 $m^2/g$, greater than 700 $m^2/g$, greater than 800 $m^2/g$, or greater than 900 $m^2/g$. In some embodiments, the BET surface area is from 400 $m^2/g$ to 1000 $m^2/g$, from 500 $m^2/g$ to 1000 $m^2/g$, from 600 $m^2/g$ to 1000 $m^2/g$, from 700 $m^2/g$ to 1000 $m^2/g$, from 800 $m^2/g$ to 1000 $m^2/g$, or from 900 $m^2/g$ to 1000 $m^2/g$.

In some embodiments, an initial concentration of one or more of C5+ or C6+ components is greater than 150 ppm, greater than 250 ppm, greater than 500 ppm, greater than 1000 ppm, greater than 2000 ppm, or greater than 3000 ppm. In some embodiments, the initial concentration is from 150 ppm to 4000 ppm, from 250 ppm to 4000 ppm, from 500 ppm to 4000 ppm, from 1000 ppm to 4000 ppm, from 2000 ppm to 4000 ppm, or from 3000 ppm to 4000 ppm. In some embodiments, the final concentration of one or more of C5+ or C6+ components is less than 30 ppm, less than 20 ppm, less than 10 ppm, less than 5 ppm, less than 4 ppm, less than 3 ppm, less than 2 ppm, or less than 1 ppm.

In some embodiments, the C6+ components comprise one or more of benzene, heptane, octane, nonane, toluene, or ethylbenzene. In some embodiments, the sorbent is adapted to remove C5+ components from the fluid volume. In such embodiments, the C5+ components comprise neopentane.

In some embodiments, the sorbent is in a form of beads that form a sorbent bed. In some embodiments, a size of the beads is from 2.4 mm to 4 mm.

In another aspect of the present disclosure, a thermal swing adsorption system comprises a sorbent bed comprising a sorbent. In some embodiments, the sorbent comprises amorphous $SiO_2$ at a weight percent greater than 80%. In some embodiments, an RMA of the sorbent is greater than 10%. In some embodiments, a total pore volume for pores between 500 nm and 20000 nm in diameter is greater than 10 $mm^3/g$.

Figure 2:
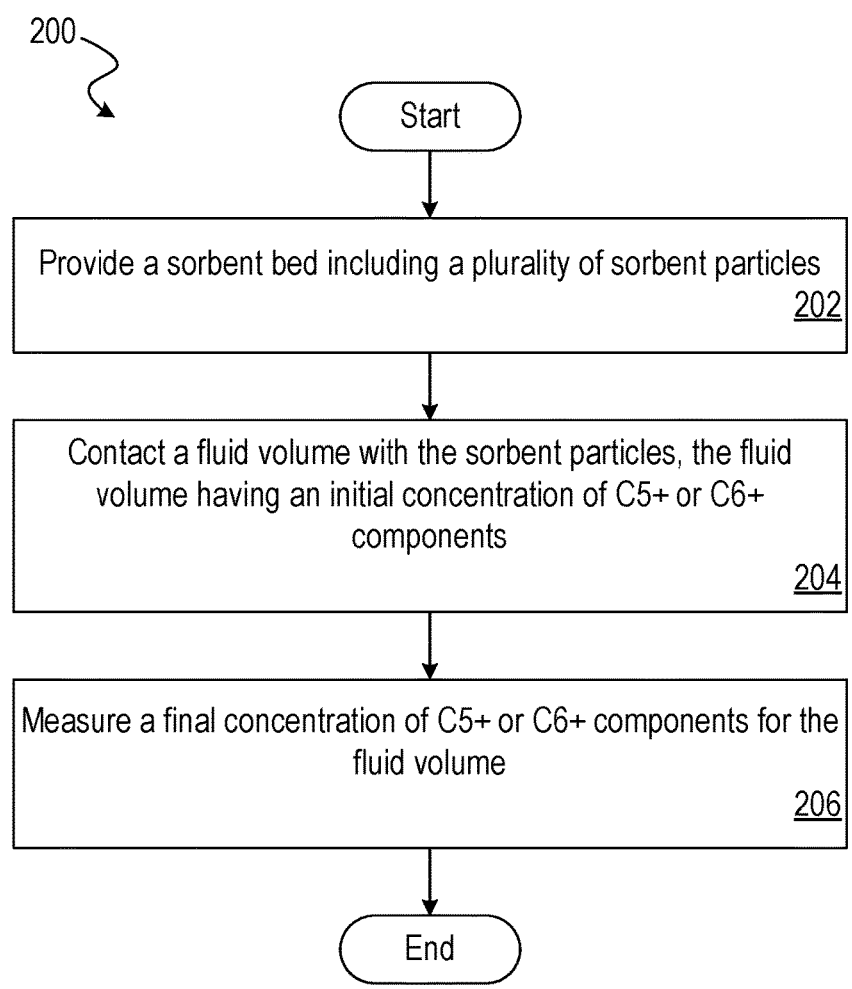
FIG. 2 illustrates a method for removing heavy hydrocarbons from a fluid volume in accordance with an embodiment of the disclosure.

FIG. 2 illustrates a method 200 for removing heavy hydrocarbons from a fluid volume in accordance with an embodiment of the disclosure. At block 202, a sorbent bed including a plurality of sorbent particles is provided. In some embodiments, the sorbent bed corresponds to the sorbent bed 110 described with respect to FIG. 1. At block 204, a fluid volume is contacted with the sorbent particles. The fluid volume may have an initial concentration of C5+ or C6+ components (e.g., a concentration of benzene and/or other components that is greater than 150 ppm). At block 206, a final concentration of C5+ or C6+ components is measured for the fluid volume. In some embodiments, the contacting occurs in a thermal swing-adsorption system.

ILLUSTRATIVE EXAMPLES

The following examples are set forth to assist in understanding the disclosure and should not, of course, be construed as specifically limiting the embodiments described and claimed herein. Such variations of the disclosed embodiments, including the substitution of all equivalents now known or later developed, which would be within the purview of those skilled in the art, and changes in formulation or minor changes in experimental design, are to be considered to fall within the scope of the embodiments incorporated herein.

Example 1: Sorbent Bed Parameters

Table 1 below illustrates parameters of exemplary sorbent beds prepared using different sorbents, in accordance with the embodiments described herein. The exemplary sorbents used were Sorbead®H and Sorbead®LE32. It is expected that heavy hydrocarbons other than benzene may be adsorbed in a similar manner under similar conditions.

TABLE 1

| Sorbent bed parameters | | | | |
|---|---|---|---|---|
|  | Sorbead ®H | Sorbead ®LE32 | Sorbead ®LE32 | Sorbead ®LE32 |
| Kg adsorbed/bed | 25,000 | 25,000 | 20807 | 12500 |
| Volume ($m^3$/bed) | 35.7 | 42.9 | 35.7 | 21.44 |
| Final benzene concentration (ppm) | 32 | 0 | 1 | 32 |
| Density (kg/$m^3$) | 700 | 583 | 583 | 583 |

Example 2: Micropore Surface Area Measurements

Two sorbents, Sorbead®LE32 and Sorbead®H, were characterized via nitrogen porosimetry using a Micromeritics ASAP® 2000 porosimetry system. The resulting data was analyzed with Micromeritics ASAP® 2010 software to determine micropore surface area and BET surface area, and is summarized in Table 2 below. Sorbead®LE32 was found to have substantially higher micropore surface area than Sorbead®H.

TABLE 2

| RMA measurements | | |
|---|---|---|
| | Sorbead ®LE32 | Sorbead ®H |
| BET surface area (m²/g) | 750 | 774 |
| Micropore surface area (m²/g) | 232 | 40 |
| RMA (%) | 31 | 5.2 |

Example 3: Pore Volume Measurements

Sorbead®LE32 and Sorbead®H were further characterized via mercury porosimetry using a Thermo Scientific Pascal 140/240 porosimeter. The resulting data was analyzed with "Pascal 140/240/440 v. 1.05" software, and is summarized in Table 3 below.

TABLE 3

| Pore volume measurements | | |
|---|---|---|
| | Sorbead ®LE32 | Sorbead ®H |
| Pore volume between 500 nm and 20000 nm (mm³/g) | 170 | 8 |

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment". "certain embodiments", or "one embodiment" in various places throughout this specification are not necessarily all referring to the same embodiment.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A method of treating a fluid volume, the method comprising contacting the fluid volume with a sorbent, wherein:
    the fluid volume has an initial concentration of C6+ components prior to the contacting,
    the fluid volume has a final concentration of C6+ components after the contacting that is less than the initial concentration of C6+ components,
    the sorbent comprises amorphous $SiO_2$ at a weight percent greater than 90%,
    a relative micropore surface area (RMA) of the sorbent is greater than 10%, and
    a total pore volume for pores between 500 nm and 20000 nm in diameter is greater than 70 mm³/g.

2. The method of claim 1, wherein the RMA of the sorbent is greater than 15%.

3. The method of claim 1, wherein the sorbent comprises a fluid-accessible surface having a Brunauer-Emmett-Teller (BET) surface area greater than 500 m²/g.

4. The method of claim 1, wherein the initial concentration of C6+ components is greater than 150 ppm, and wherein the final concentration of C6+ components is less than 30 ppm.

5. The method of claim 1, wherein the C6+ components comprise one or more of benzene, heptane, octane, nonane, toluene, or ethylbenzene.

6. The method of claim 1, wherein the sorbent is adapted to remove C5+ components from the fluid volume, wherein the C5+ components comprise neopentane.

7. The method of claim 1, wherein the sorbent is in a form of beads that form a sorbent bed, wherein a size of the beads is from 2.4 mm to 4 mm.

8. The method of claim 1, wherein the contacting occurs in a thermal swing-adsorption system.

9. A method of treating a fluid volume, the method comprising contacting the fluid volume with a sorbent, wherein:
    the fluid volume has an initial concentration of C6+ components prior to the contacting,
    the fluid volume has a final concentration of C6+ components after the contacting that is less than the initial concentration of C6+ components,
    the sorbent comprises amorphous $SiO_2$ at a weight percent greater than 90%,
    a total pore volume for pores between 500 nm and 20000 nm in diameter is greater than 100 mm³/g, and
    an RMA of the sorbent is greater than 15%.

10. The method of claim 9, wherein the sorbent comprises a fluid-accessible surface having a Brunauer-Emmett-Teller (BET) surface area greater than 500 m²/g.

11. The method of claim 9, wherein the initial concentration of C6+ components is greater than 150 ppm, and wherein the final concentration of C6+ components is less than 30 ppm.

12. The method of claim 9, wherein the C6+ components comprise one or more of benzene, heptane, octane, nonane, toluene, or ethylbenzene.

13. The method of claim 9, wherein the sorbent is in a form of beads that form a sorbent bed, wherein a size of the beads is from 2.4 mm to 4 mm.

14. The method of claim 9, wherein the contacting occurs in a thermal swing-adsorption system.

15. A thermal swing adsorption system comprising a sorbent bed comprising a sorbent, the sorbent comprising amorphous $SiO_2$ at a weight percent greater than 90%, wherein a relative micropore surface area (RMA) of the sorbent is greater than 10%, and wherein a total pore volume for pores between 500 nm and 20000 nm in diameter is greater than 70 mm³/g.

16. The thermal swing adsorption system of claim 15, wherein the thermal swing adsorption system is adapted for adsorption of C6+ components from a fluid volume, wherein the C6+ components comprise one or more of benzene, heptane, octane, nonane, toluene, or ethylbenzene.

17. The thermal swing adsorption system of claim 15, wherein the thermal swing adsorption system is adapted to remove C5+ components from a fluid volume, wherein the C5+ components comprise neopentane.

* * * * *